United States Patent [19]
Jeromin et al.

[11] Patent Number: 5,661,309
[45] Date of Patent: Aug. 26, 1997

[54] ELECTRONIC CASSETTE FOR RECORDING X-RAY IMAGES

[75] Inventors: Lothar Siegfried Jeromin, Newark, Del.; Denny Lap Yen Lee, West Chester, Pa.; Edward Neill Lawrence, Wilmington, Del.

[73] Assignee: Sterling Diagnostic Imaging, Inc., Newark, Del.

[21] Appl. No.: 995,729

[22] Filed: Dec. 23, 1992

[51] Int. Cl.$^6$ ..................................................... G01T 1/24
[52] U.S. Cl. ..................... 250/580; 250/370.09; 378/189
[58] Field of Search ................................. 378/189, 182, 378/183; 250/589, 580, 370.09

[56] References Cited

U.S. PATENT DOCUMENTS

| | | | |
|---|---|---|---|
| 3,973,146 | 8/1976 | Arnold et al. | 257/254 |
| 4,134,137 | 1/1979 | Jacobs et al. | |
| 4,670,765 | 6/1987 | Nakamura et al. | 307/311 |
| 4,672,454 | 6/1987 | Cannella et al. | 358/213.11 |
| 4,694,317 | 9/1987 | Higashi et al. | 257/446 |
| 4,857,723 | 8/1989 | Modisette | 250/213 R |
| 4,861,995 | 8/1989 | Ohgoda | 250/589 |
| 4,931,643 | 6/1990 | Amtmann | 250/583 |
| 4,961,209 | 10/1990 | Rowlands et al. | 378/29 |
| 4,975,935 | 12/1990 | Hillen et al. | 378/28 |
| 5,070,248 | 12/1991 | Pesce | 250/483.1 |
| 5,127,038 | 6/1992 | Jeromin et al. | 378/28 |
| 5,166,524 | 11/1992 | Lee et al. | 250/580 |
| 5,168,160 | 12/1992 | Jeromin et al. | |
| 5,182,624 | 1/1993 | Tran et al. | 257/40 |

FOREIGN PATENT DOCUMENTS

| | | |
|---|---|---|
| 0 125 691 | 11/1984 | European Pat. Off. |
| 63-3454 | 1/1988 | Japan. |

OTHER PUBLICATIONS

L. E. Antonuk et al., "Development of Hydrogenated Amorphous Silicon Sensors for High Energy Photon Radiotherapy Imaging", Nuclear Science vol. 37, No.2, Apr. 1990 pp. 165–170.

L. E. Antonuk et al., "Development of Hydrogenated Amorphous Silicon Sensors For Diagnostic X–Ray Imaging", Nuclear Science vol. 38, No. 2, Apr. 1991, pp. 636–640.

L. E. Antonuk et al., "Signal, Noise, and Readout Considerations in the Development of Amorphous Silicon Photodiode Arrays for Radiotherapy and Diagonstic X–Ray Imaging", SPIE vol. 1443 Medical Imaging V. Image Physics 1991, pp. 108–119.

L. E. Antonuk et al., "Development Of Thin–Film, Flat–Panel Arrays For Diagnostic And Radiotherapy Imaging", SPIE Medical Imaging VI, Feb. 23–27, 1992.

W. Zhao et al., "A Large Area Solid–State Detector For Radiology Using Amorphous Selenium", Medical Physics Research.

L. E. Antonuk et al., "Large Area Amorphous Silicon Photodiode Arrays For Radiotherapy And Diagnostic Imaging", Nuclear Instruments and Methods in Physics Research A310 (1991) pp. 460–464.

*Primary Examiner*—Constantine Hannaher
*Attorney, Agent, or Firm*—Ratner & Prestia

[57] ABSTRACT

An electronic cassette contains an X-ray image capturing panel comprising a solid state transistor array and storage capacitors on which is built a layered structure including a photoconductive layer. The storage capacitors capture electrical charges generated in the photoconductive layer by incident X-radiation and the image-wise charges are read out by the transistor array. The cassette contains an internal power supply and a built-in image storage medium among a plurality of electronic components to allow self-contained operation and temporary recording of digitized values which are representative of the pattern of incident X-radiation.

13 Claims, 7 Drawing Sheets

ELECTRONIC CASSETTE FOR RECORDING X-RAY IMAGES

BACKGROUND OF THE INVENTION

1. Field of the Invention

This invention pertains to capturing X-ray images and, more particularly, to a filmless, self-contained, portable electronic cassette and associated process for capturing and recording digital representations of radiographic images.

2. Description of the Related Art

Well known medical diagnostic processes record X-ray images on silver halide-based films. These systems generally require directing a beam of X-radiation through the subject to be studied, intercepting the beam with an image intensifying element, recording the intensified and imagewise modulated beam in a silver halide based film, and chemically transforming this captured latent image into a permanent and visible image, called a radiogram. See U.S. Pat. No. 5,070,248, titled CASSETTE WITH INTENSIFYING SCREENS TO BE USED WITH AN X-RAY FILM. Significant progress has been made in this area by increasing the effectiveness of the intensifying screen to reduce patient X-ray exposure levels, packaging the system so it can be used in daylight conditions, and creating digitized representations of the image that can be manipulated and interpolated in a multitude of ways to aid in interpretation of the recorded image. It would be desirable to eliminate the expense and time consumed by use of film sheets and chemical processing.

Progress has been made in introducing systems that do not on traditional silver halide-based films. The radiography process captures a latent radiographic image using a photoconductive layer sensitive to X-radiation (L. Jeromin, "Electroradiography", in Encyclopedia of Medical and Instrumentation, edited by J G Webster, Wiley, New York, 1988). Before exposure to X-radiation, the surface of the photoconductive layer is uniformly charged; after exposure to X-radiation, depending on the intensity of the imagewise modulated radiation, electron-hole pairs generated by the X-radiation are separated by an electric field incident to the charges laid over the surface and move along the field to recombine with the surface charge. After X-ray exposure, a latent image in the form of electrical charges of varying magnitude remain on the plate surface and may be rendered visible by toning and transferring the image to a receiving sheet.

Efforts to eliminate the recording film also include using a layer of stimulable phosphor to intercept the radiation transmitted image. See, for example, U.S. Pat. No. 4,931,643, AUTORADIOGRAPHY SYSTEM FOR STIMULABLE PHOSPHOR FOILS. The phosphor is chosen such that it emits light corresponding to the latent image stored therein when subsequently scanned with stimulating rays. Such systems generally employ a recording apparatus for storing the image in the stimulable phosphor, a radiation image read-out apparatus for reading out the image stored on the stimulable phosphor, and frequently, image reproducing apparatus. These are usually provided independently of one another, so that size and manufacturing costs remain large. One improvement on this approach is described in U.S. Pat. No. 4,975,580, RADIATION IMAGE READ-OUT AND REPRODUCING APPARATUS, wherein the image read-out and reproduction are carried out by use of the same scanning system. Further, means for conveying the stimulable phosphor sheet for read-out and for conveying the recording sheet for reproducing are common to one another. However, resolution of the image is degraded because of light-scattering in the storage phosphor.

These systems for using silver-halide based films, xeroradiography or stimulable phosphors suffer common problems since: (1) the image cannot be obtained immediately after exposure as time is consumed during transport of the cassette to the film processor and during subsequent film processing operations; (2) considerable time and equipment is required to load and unload un-reuseable films from cassettes and to develop films into radiograms; and, (3) the medically valuable information is not in a format that can readily provide a digital output if image processing is used to enhance diagnostic analysis. It is therefore desirable to be able to directly record radiograms in a digital format, without further processing shortly after exposure, and to also eliminate the equipment used for loading, unloading, and developing traditional X-ray film based systems and reuseable phosphor screen systems.

Efforts to overcome these deficiencies include the use of an electrostatic panel comprising a photoconductive layer over an insulating layer on a conductive support, the photoconductive layer also covered by a dielectric layer, the dielectric layer overcoated with a plurality of microplates that form a microcapacitor structure. Improvements in this method, involving the use of a plurality of thin-film transistors interconnected with a network of conductive lines orthogonal to one another to further increase the resolution, have been described in a co-pending application, Docket No. IM-0817, also assigned to Du Pont.

SUMMARY OF THE INVENTION

The present invention provides an easily transported electronic cassette and process whereby radiograms are captured as an electronic charge distribution which is subsequently digitized within a single image capture panel which is contained in the electronic cassette. The cassette has integral means both for power and for memory of digitized electronic charge distribution formed during multiple radiograms, thereby allowing the cassette to be freely moveable between locations in a radiology department. Unique to this invention is the integration of several elements in such a way that digital radiograms can be obtained without disrupting the normal routine in radiology departments.

In its process of use, the electronic cassette receives a first imagewise modulated X-ray pattern, whereby the image capture panel is exposed through the cassette. An image capture panel converts the impinging radiation into electrical charges that are converted by a matrix of electrical devices into a plurality of digitized picture element values, which values are stored in a predetermined orderly manner in electronic memory storage means located within the electronic cassette. The image capture panel is erased and then the electronic cassette receives a second imagewise modulated X-ray pattern in a second position relative to a patient. The electronic cassette may be transported to another location whereat the process is repeated with the same or a different patient. These digitized picture element values, representative of several different radiograms, are then transferred from the memory means through an electronic connector integral with the cassette to any of many different external systems for recording digital data, computer-processing of the digital data and converting the digitized picture element values into visible images.

DETAILED DESCRIPTION OF THE PREFERRED EMBODIMENT

Figure 1:
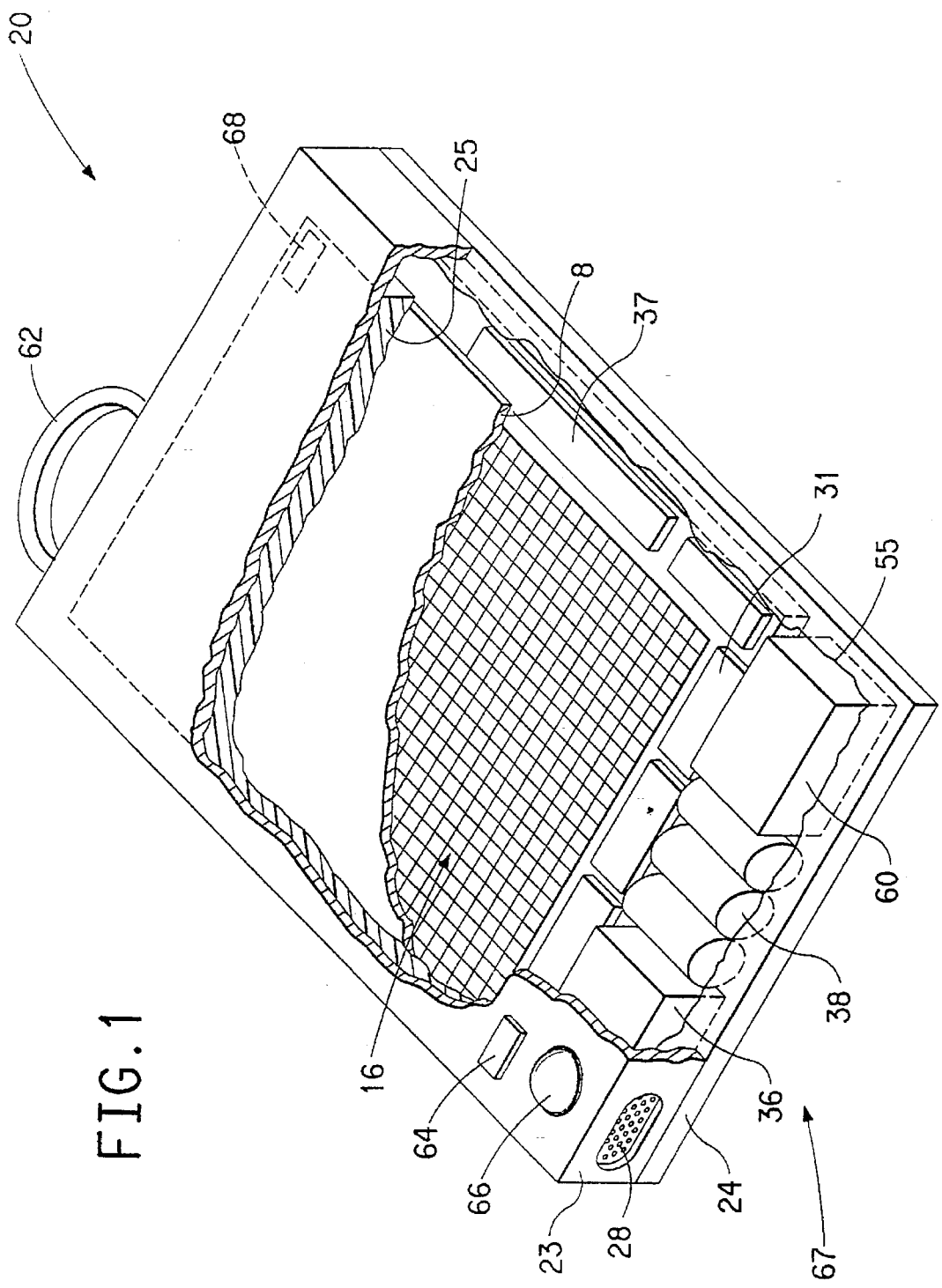
FIG. 1 is a perspective view of an electronic cassette in accordance with the present invention.

FIG. 1 shows an electronic cassette 20 formed by front and back members 23 and 24, respectively, connected to form a container allowing assembly and access to internally placed elements in which an X-ray image capture panel 16 is placed. The image capture panel 16 is capable of capturing a plurality of electrical charges representative of imagewise modulated radiation. Because of its manner of use, wherein a portion of a patient's body is frequently placed atop the cassette and the cassette is routinely moved about in a hospital examining environment, it is important that the front and back members 23 and 24 are fabricated using materials capable of withstanding weight densities up to 5 pounds per square inch, such as carbon-fiber laminates which are substantially transparent to X-rays. Similarly, a design of construction of the cassette is chosen to impart protection from handling damage during frequent movements and possible accidental mishaps, including a load-distributing member 25 made, for example, from a low-density polyurethane foam. Located in the cassette 20 are electronic converting means that convert the plurality of electrical charges into a plurality of digitized picture element values, which values are stored in a predetermined orderly manner in electronic memory storage means located within the electronic cassette. These electronic elements are part of an electronic system 67 comprising a CPU 60, a memory storage means 36, readout electronics 31, addressing electronics 37, a sensor 68 capable of detecting the presence and absence of X-rays that occurs when image-wise radiation impinges onto the cassette 20 or when image-wise radiation is removed from the cassette 20, an electronic connector 28 to connect the cassette 20 to external electronic systems for readout or display of image data retained in memory, and a ready-light 66 that alerts the operator that the cassette is in condition to receive X-radiation. The plurality of small electrical charges captured in the image capture panel 16 is measured and then transferred from the the image capture panel 16 to memory storage means 36 before the image capture panel 16 is erased, or made uniform, by the application of a reversing bias signal, prior to a second exposure to imagewise modulated radiation. In the present invention, an important feature is a self-contained, battery-like power supply 38 inside the cassette 20 enabling the cassette 20 to be used independently of external power sources and also being easily transported between locations in a hospital, for example. The front member 23 of the cassette 20 is made of material which is transparent to X-rays, but opaque to low-energy radiation so that it shields the panel 16 from exposure, much in the manner a conventional medical cassette shields an X-ray film. A plastic such as polymethylmethacrylate is one such material. By low-energy radiation, for purposes of describing the present invention, is meant ultraviolet, infrared, or visible radiation, but excludes X-radiation and gamma-radiation.

Figure 2A:
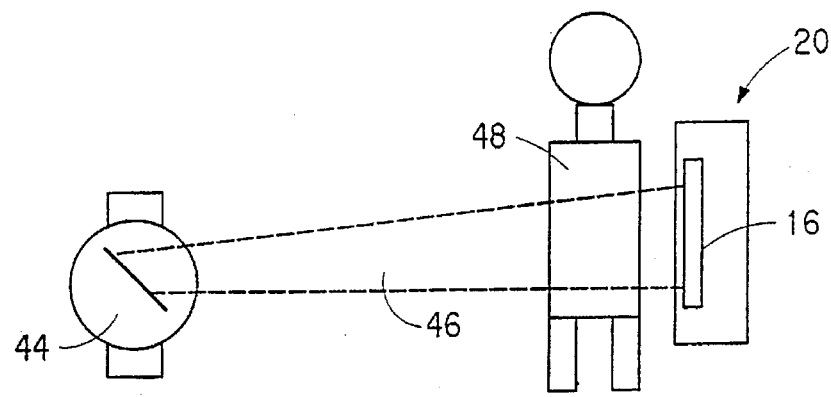
FIGS. 2a, 2b, and 2c are schematic elevation views of an arrangement for using an electronic cassette in accordance with the present invention for capturing an X-ray image.

FIG. 2a shows the electronic cassette 20 in its process of use. The electronic cassette 20 is placed by an operator, generally a medical technician, in a first position much like a standard screen-film cassette is used to receive a first imagewise modulated X-ray pattern. A patient 48, i.e., in the case of medical diagnostic imaging, is positioned in an X-ray beam path emitted by a source 44 of X-radiation. The emerging radiation 46 through the patient 48 is intensity modulated because of the different degree of X-ray absorption in the patient 48.

Figure 3:
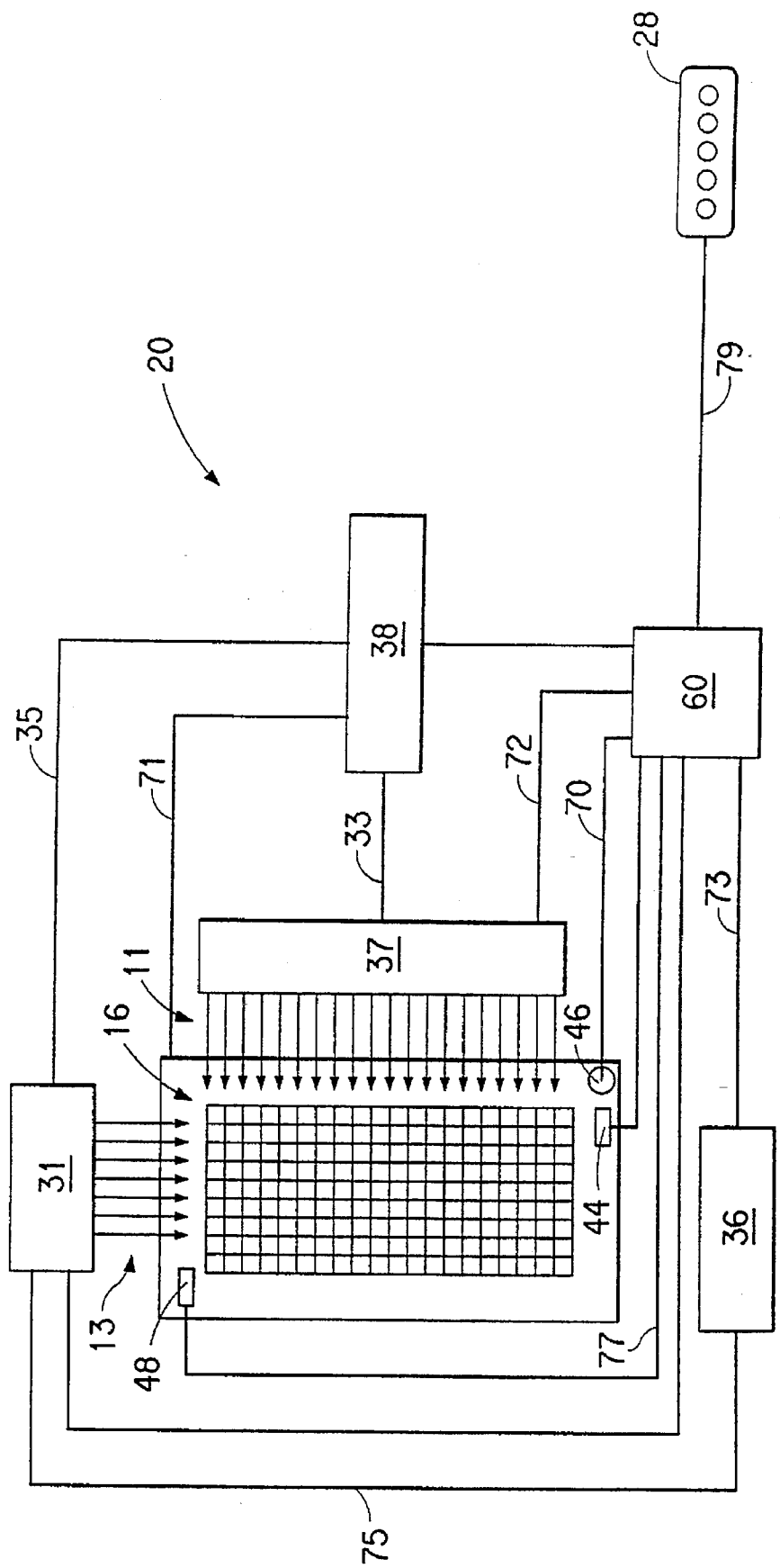
FIG. 3 is a schematic plan view of the electronic cassette shown in FIG. 1.

FIG. 3 illustrates schematically the essential features of the cassette. An activating switch 64 located on the exterior of the cassette 20 provides operating power from power supply 38 to the electronic system 67 within the cassette 20. A CPU 60 causes power to be supplied to the image capture panel 16 from the power supply 38 over line 71 and also activates the electronic system 67 associated with the image capture panel 16, shown in greater detail in FIG. 6. The ready-light 66 is activated when the image capture panel 16 is in condition to receive X-radiation. The impinging radiation is converted to a plurality of electrical charges by the image capture panel 16. When the X-ray sensor 68 senses the presence of X-radiation followed by the absence of X-radiation, a process of digitizing the plurality of electrical charges begins. This plurality of charges is converted within the readout electronics 31 shown later in greater detail in FIG. 6 to produce a plurality of digitized image element values, and these values are transferred over line 75 in a predetermined orderly manner to electronic memory storage means 36 which could be solid-state memory circuits or a miniature magnetic or optical digital recorder located within the electronic cassette 20. During this time, the ready-light is inactivated since the cassette is not in condition to record an X-radiation pattern. When it is desired to read out the radiogram recorded in memory storage means 36, the digitized image element values are directed over line 73 to the CPU 60 and then directed over line 79 to the connector 28 on the electronic cassette 20. The self-contained electronic memory storage means 36 is an important feature of the present invention because it facilitates free movement of the electronic cassette 20 between different X-ray imaging positions and additionally enables the operator to make multiple X-radiation exposures without having to first transfer prior radiation pattern information to external sources. After the digitized image element values are stored in memory, CPU 60 causes the image capture panel 16 to be erased in preparation for capturing a subsequent radiogram using a process described elsewhere herein. It is also necessary to identify the patient, which can be done by using the connector 28 to supply identification data to the memory storage means 36 in correspondence with the digitized image element values belonging to that patient.

Figure 2B:
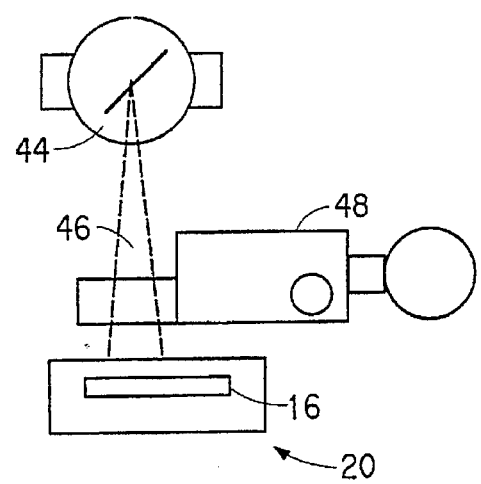
Figure 2C:
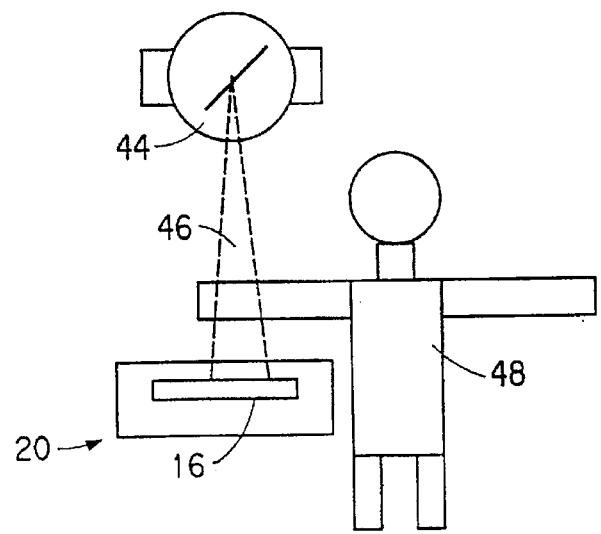

The ready light 66 is activated by a signal over line 70 from the CPU 60 to indicate to the operator that the first imagewise modulated radiation pattern has been captured and the image capture panel 16 has been erased. The technician then places the electronic cassette 20 in a second position relative to the patient 48 as illustrated in FIG. 2b without removing the image capture panel from the cassette for processing or data readout. A handle 62 is attached to the cassette 20 to facilitate hand movement of the cassette between radiation exposing positions. Of course, if no additional medical information was desired from the first target, the electronic cassette could be similarly used with a second target, again without the necessity of removing the image capture panel from the cassette for processing. When the electronic cassette 20 is in the second position to receive a second imagewise modulated x-ray pattern, the X-ray image capture process is repeated, except that the digitized image element values of the second exposure are stored separately from the first set of digitized picture element values, but within the same memory storage means 36. This process is repeated until all desired exposures have been completed, for a single or several targets, as illustrated in FIG. 2c and the series of radiation exposures have been converted into digitized picture element values captured within the electronic cassette 20. Because the image capture panel has not required processing steps between exposures, and because it is possible to take various types of radiograms without moving the patient between different rooms having different radiographic processes, the efficiency of the overall radiographic process is increased. Because this process of use requires unconstrained relocation of the cassette and multiple capture of radiograms using the cassette without interruptions for further processing, the above described self-contained memory storage means 36 and power supply 38 are essential elements of this invention.

Figure 4:
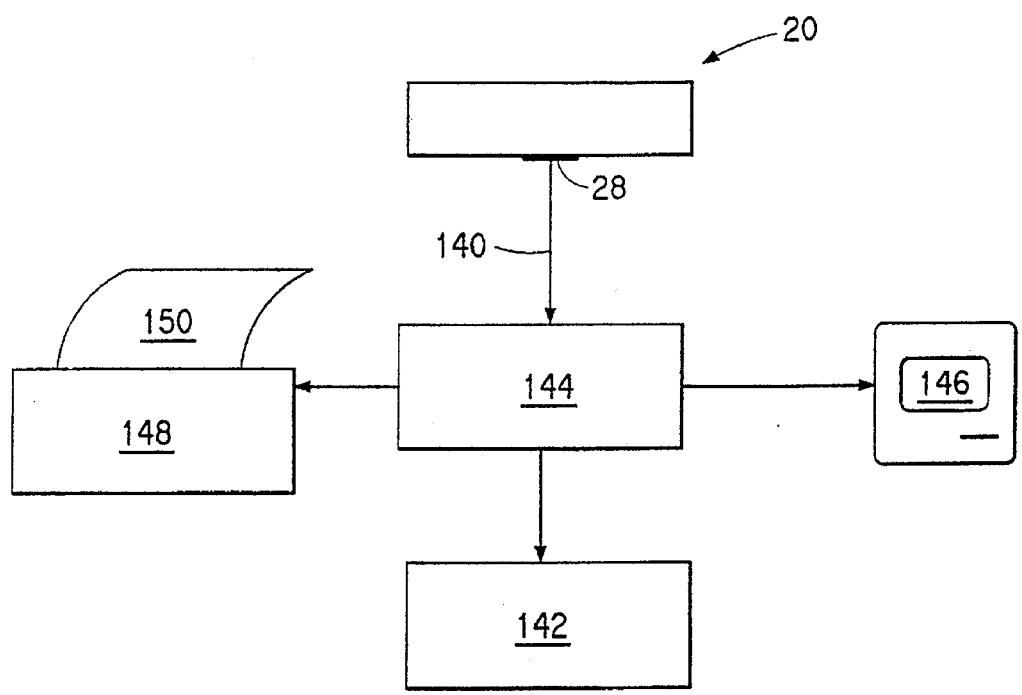
FIG. 4 is a block diagram of an arrangement for the capture and display of a radiogram using an electronic cassette in accordance with the present invention.

FIG. 4 shows the digitized picture element values obtained from the electronic cassette 20 using connector 28 and directed to a computer 144. Computer 144, inter alia, directs the signal to appropriate storage means which may be an internal RAM memory within a host computer or a long term archive memory 142 or both. In the process, the data representing the radiogram may undergo image processing, such as filtering, contrast enhancement by many different external systems for permanently recording digital data, modifying the data to facilitate interpretation and converting the digitized picture element values into visible images, and may be displayed on a CRT 146 for immediate viewing or used in a printer 148 to produce a hard copy 150.

It is also possible to send the plurality of electrical charges captured by the image capture panel to external means for digitizing and storing the image data and to provide operating power using connector 28, if, for example, lower cost designs of an image capturing cassette were desired. In such a lower cost design, the power and memory means could be supplied using a cable available in several different room within a hospital, the cable providing access to a common power and memory means.

Figure 5:
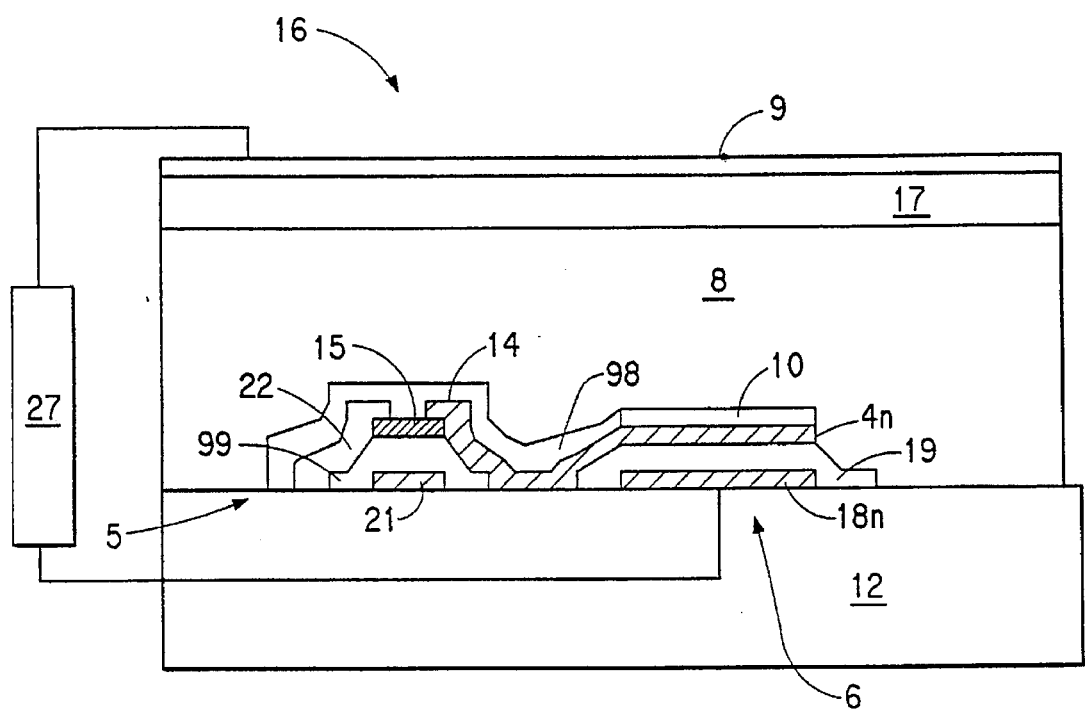
FIG. 5 shows a schematic cross sectional elevation view of a portion of an X-ray image capture panel in accordance with the present invention.

FIG. 5 shows an X-ray image capture panel 16 having a dielectric substrate layer 12 with a thickness to give the panel 16 a rigidity necessary for handling. A preferred material for the substrate layer 12 is glass. Over the dielectric substrate layer 12 is a first plurality of discrete minute conductive electrodes 18 (ie., 18a, 18b, 18c, . . . 18n) referred to herein as outer microplates 18n. Preferably, the outer microplates 18n are made of aluminum. The technology to produce such outer microplates 18n is well known in the art. The dimensions of the outer microplates 18n define the smallest picture element (pixel) resolvable by the element 16. They are deposited on the substrate dielectric layer 12, typically, though not necessarily, using thermal deposition or sputtering techniques and can be made of a very thin-film of metal such as gold, silver, copper, chromium, titanium, platinum and the like. Alternatively, a conductive material such as indium-tin-oxide may be used. Over this first plurality of outer microplates is applied a dielectric material 19, preferably comprised of silicon dioxide; other materials such as silicon nitride may be used. Also deposited on the dielectric substrate layer 12 is a plurality of transistors 5 having two electrodes 22 and 14 and a gate 21. Further shown in FIG. 5 is a second plurality of microplates 4 (ie., 4a, 4b, 4c, . . . 4n) referred to herein as inner microplates 4n which form a plurality of capacitors 6 with the outer microplates 18n and dielectric material 19. They are deposited on the dielectric substrate layer 12 typically, though not necessarily, using vacuum thermal deposition or sputtering techniques, and can be made of a very thin-film of metal such as gold, silver, copper, chromium, titanium, platinum and the like. Preferably, the outer microplates 18n are made of aluminum or indium-tin oxide.

Figure 6:
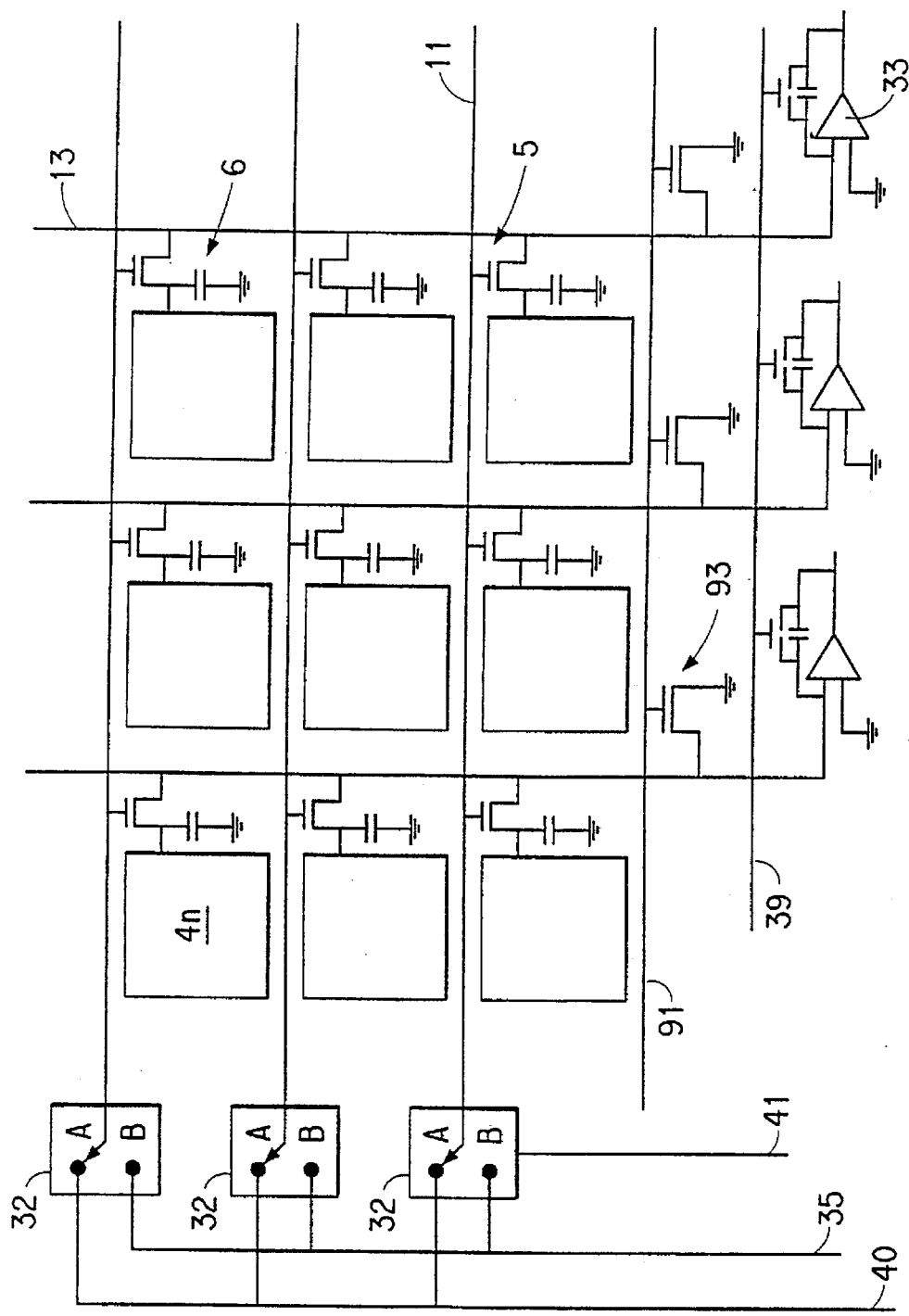
FIG. 6 is a schematic top view of the X-ray image capture panel shown in FIG. 1.

FIG. 6 shows at least one transistor 5 connecting each capacitor 6 to an Yn line 13. Each transistor 5, typically a field-effect transistor, has its gate connected to an Xn line 11 and its source or drain connected to a Yn line 13. A charge storage capacitor 6 is formed by the inner microplates 4n, outer microplates 18n, and the dielectric material 19. Each inner microplate 4n is also connected to electrode 14 of transistor 5. Each outer microplate 18n is connected to electrical ground. Each transistor 5 serves as a bi-directional switch allowing current flow between the Yn line 13 sense lines and the charge storage capacitor 6 depending on whether a bias voltage is applied to its gate through Xn address lines. The transistor 5 preferably comprises a hydrogenated amorphous-silicon layer 15, an insulating layer 99, a conductive gate 21 and the two conductive electrodes, one electrode 22 being connected to the Yn sense lines 13 and the other electrode 14 to the inner microplates 4n, as schematically depicted in FIG. 5. Each transistor could also use crystalline silicon, polycrystalline silicon or cadmium selenide. Each transistor 5 is also covered with a passivation layer 98 and can be shielded from low energy radiation using a dielectric substrate layer 12 or by using additional layers. By low energy radiation, for purposes of describing the present invention, is meant ultraviolet, infrared, or visible radiation, but excludes X-radiation and gamma-radiation. The technology for the creation of the transistors 5 and charge storage capacitors 6 is well known in the art and not a subject of the present invention. See, for instance, "Modular Series on Solid State Devices," Volume 5 of Introduction to Microelectronics Fabrication by R. C. Jaeger, Published by Addison-Wesley in 1988.

In the spaces between the microplates 4a, 4b, 4c . . . 4n, conductive electrodes or X1, X2, . . . Xn address lines 11 and conductive electrodes or Y1, Y2, . . . Yn sense lines 13 are laid out. The Xn lines 11 and Yn lines 13 lines are shown laid out generally orthogonally to each other in the spaces between the inner microplates 4n. The orientation of the Xn lines 11 and Yn lines 13 is a matter of choice. The Xn address lines 11 are individually accessible through leads or connectors not specifically illustrated in the drawings, along the sides or edges of the panel 16.

For fabrication purposes, the Xn lines 11 and Yn lines 13 may be constructed from the same aluminum layer used for fabricating the inner microplates 4n. Since the Xn lines 11 and Yn lines 13 must not electrically contact each other where they cross over, the Yn lines 13 may be created after placing an insulating layer not shown in the figure over the Xn lines 11.

Each Yn line 13 is also typically connected to readout electronics 31 which may comprise a charge amplifier 33 wired to measure the charge in a capacitive circuit to which the charge from the storage capacitor 6 is directed. The output of the charge amplifier 33 may be digitized, for instance by using A/D converters, and sampled sequentially to obtain an output signal and the technology to do this is also well known in the art.

Over the top surface of the inner microplates 4n there is applied a charge blocking layer 10. The charge blocking layer 10 is preferably provided by an aluminum oxide layer formed on the surface of the inner microplates 4n although other blocking interfaces may also be used. The subsequent coating thereon of a selenium photoconductive layer 8 produces an X-ray absorption layer. In addition, the combination of layers 4n, 10, and 8 behaves as a blocking diode, inhibiting one type of charge flow in one direction. The charge blocking layer 10 must have sufficient thickness to prevent charge leakage. In the preferred embodiment of the present invention, charge blocking layer 10 should have a thickness greater than 100 Angstroms (0.01 micrometer).

Coated over the charge blocking layer 10, the transistors 5, and the gate and sense lines, is a photoconductive layer 8 having a back surface in contact with the inner microplates 4n, and a front surface. The photoconductive layer 8 preferably exhibits very high dark resistivity and may comprise amorphous selenium, lead oxide, cadmium sulfide, mercuric iodide or any other such material, including organic materials such as photoconductive polymers preferably loaded with X-ray absorbing compounds, which exhibit photoconductivity.

In the context of the present invention, exhibiting photoconductivity means that upon exposure to X-radiation, the photoconductive material exhibits reduced resistivity relative to that in the absence of such exposure. The reduced resistivity is in reality the effect of electron hole pairs generated in the material by the incident radiation. Because the capacitive time constant of a capacitor is proportional to the resistance of the capacitor, the capacitor formed by such photoconductive material has a reduced time constant upon exposure.

The photoconductive layer 8 should be chosen of sufficient thickness to absorb the incident X-radiation, or a substantial portion thereof, to provide high efficiency in radiation detection. The specific type of material selected will further depend upon the desired charge generation efficiency and charge transport property, and the desired simplicity of manufacture. Selenium is one preferred material.

A dielectric layer 17 is added on the top front surface of the photoconductive layer 8. In the preferred embodiment of the present invention, dielectric layer 17 should have a thickness greater than one micron. Mylar® (i.e., polyethylene terephthalate) film with a thickness of 25 micrometers may be used for layer 17, although layers of other thicknesses are suitable. A final front layer 9 of conductive material, such as indium-tin oxide being substantially transparent to X-radiation is formed over the dielectric layer 17.

The dielectric layer 17, the photoconductive layer 8 and the charge storage capacitors 6n form three microcapacitors in series. A first microcapacitor is created between the front conducting layer 9 and the front surface of the photoconductive layer 8, and a second microcapacitor between that same photoconductive layer 8 and the inner microplates 4n, and the third capacitor being the charge storage capacitor 6n formed between the inner microplates 4n and the outer microplates 18n.

The entire element 16 can be made by depositing successive layers of conductors 18n, insulator 19, inner microplates 4n, blocking layer 10, photoconductor 8, insulator 17, and conductor 9 upon a dielectric substrate layer 12. The FETs 5 are built in the spaces between the outer microplates 18n on the dielectric substrate layer 12. Fabrication may be accomplished by plasma-enhanced chemical vapor deposition, vacuum deposition, lamination, sputtering or any other known technique useful to deposit even thickness films.

In practice, a panel 16 may be fabricated beginning with a commercially available thin-film transistor panel which comprises a dielectric substrate layer 12, transistors 5 and Xn lines 11 and Yn lines 13. Commercially available panels used in making liquid crystal displays are a convenient starting point for building the panel 16 in accordance with the present invention. Charge storage capacitors 6 are formed by the inner and outer microplates 4n and 18n with a dielectric material therebetween, all disposed between the Xn lines 11 and Yn lines 13. The photoconductive layer 8 is coated over the charge blocking layer 10. The dielectric layer 17 and top conductive layer 9 are formed on the photoconductive layer 8 to complete the panel 16.

In a preferred embodiment, the conductive top layer 9, the dielectric layer 17, and the photoconductive layer 8 are continuous layers. However, it is within the contemplation of the present invention for one or more of the layers overlying the outer microplates 18n to comprise a plurality of discrete portions, formed in registration, for instance, by etching.

In FIG. 6, the Xn lines 11 terminate to a switching means comprising a first plurality of switches 32 that allow switching the Xn lines 11 to a first position A, and a second position B. Preferably, the switching means comprise electronically addressable solid state switches which may be either external or integral with the element 16. A bias voltage is applied over line 40 to all Xn lines 11 simultaneously when the Xn lines 11 are in the first position A. The bias voltage on the Xn lines 11 is applied to the gates of all the transistors 5 to change the transistors 5 to a conductive state to allow current to flow between source and drain.

When the switches 32 are in the second position B, lines Xn 11 are independently addressable over lines 35 and are no longer interconnected. Means to effectuate such sequential switching are not shown. Such means are well known in the art and not of particular importance to this invention as any convenient switching arrangement may be selected without altering the scope of this invention. Switches 32 may be controlled by line 41.

In FIG. 6, in addition to the circuitry discussed above connected to the panel 16, Xn addressing lines 11, and Yn sensing lines 13, there is an additional connection provided for accessing the front conductive layer 9 and the first plurality of outer microplates 18n in order to electrically connect the front conducting layer 9 and the first plurality of outer microplates 18n to a power supply 38 capable of providing a programmable series of variable voltages.

In operation, the switches 32 are first placed in position A where a bias voltage, typically 5 volts, is simultaneously applied to all Xn lines 11. In addition, a voltage of typically 5 volts is applied to an array reset line 91 causing all array reset transistors 93 to become conductive. All charge storage capacitors 6 are electrically shorted to ground through the array reset transistors. Also, all charge amplifiers 33 within the readout electronics 31 are reset through line 39. An initial operating DC voltage such as 1000 v is applied at a controlled rate to the top conducting layer 9.

Figure 7:
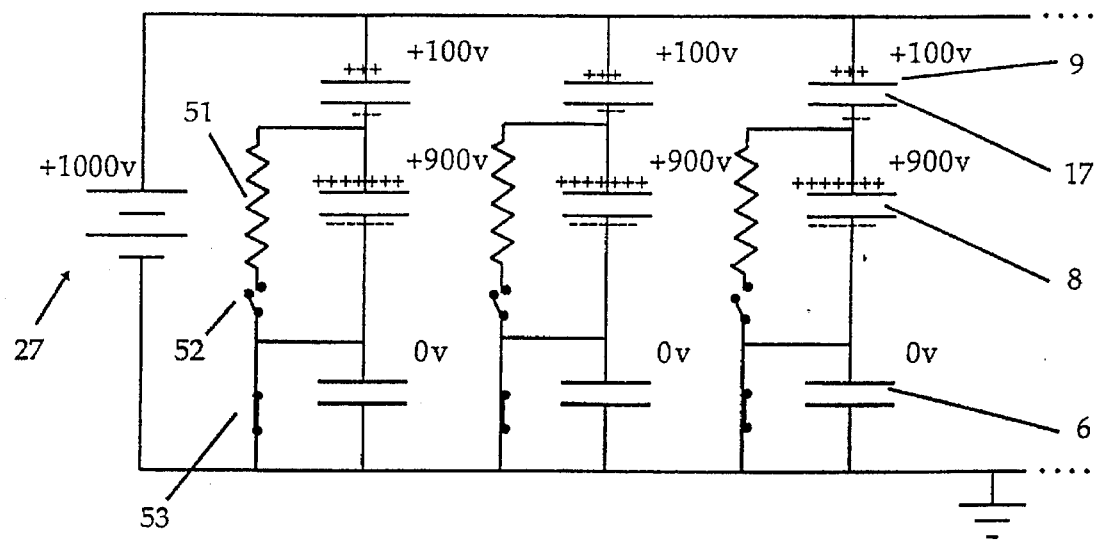
FIG. 7 represents an electrical equivalent of an X-ray image capture panel in accordance with this invention after an initial operating bias voltage is applied, prior to exposure to X-radiation.

FIG. 7 is a simplified equivalent electric circuit of the dielectric layer 17, the photoconductor layer 8 and the charge storage capacitor 6 forming three microcapacitors in series before application of the impinging radiation. In parallel with the photoconductor 8, there is shown a switch 52 and a resistor 51 representing the effect of the electron hole pair generation and transport in the photoconductive layer 8 on the capacitance of that capacitor to be described next. Before exposure to radiation, the resistance of the photoconductive material is effectively infinite; in schematic, then, equivalent to an open switch and the discharging resistor is not effective. During exposure, the resistance of the photoconductive material is lowered, equivalent to a closed switch putting the discharging resistor in parallel with the photoconductive capacitor. Preferably, the charges moving across the photoconductive layer are directly proportional to the intensity of the incident radiation.

When an initial positive operating voltage is connected across the element 16, in the absence of X-radiation, and with transistors 5 and array reset transistors 93 turned to a conductive state, the equivalent of closing the switch 53, no charge will be accumulated in the charge storage capacitors 6. In the described structure, this will result in two different voltages appearing across the capacitors, one across the microcapacitors representing the photoconductor layer 8, and the second across the microcapacitors representing the dielectric layer 17. If, for instance, the applied voltage source 27 is 1000 volts as illustrated in FIG. 7, it could be distributed across the two capacitors as 100 volts across the dielectric 17, and 900 volts across the photoconductor 8. Upon stabilization of the electric field, the voltage on the Xn lines biasing the transistors 5 is changed to a second operating voltage causing the transistors to become non-conductive, by placing switches 32 in position B. The array reset transistors 93 are also caused to become non-conductive by a similar process. This is equivalent to opening the switch 53.

Figure 8:
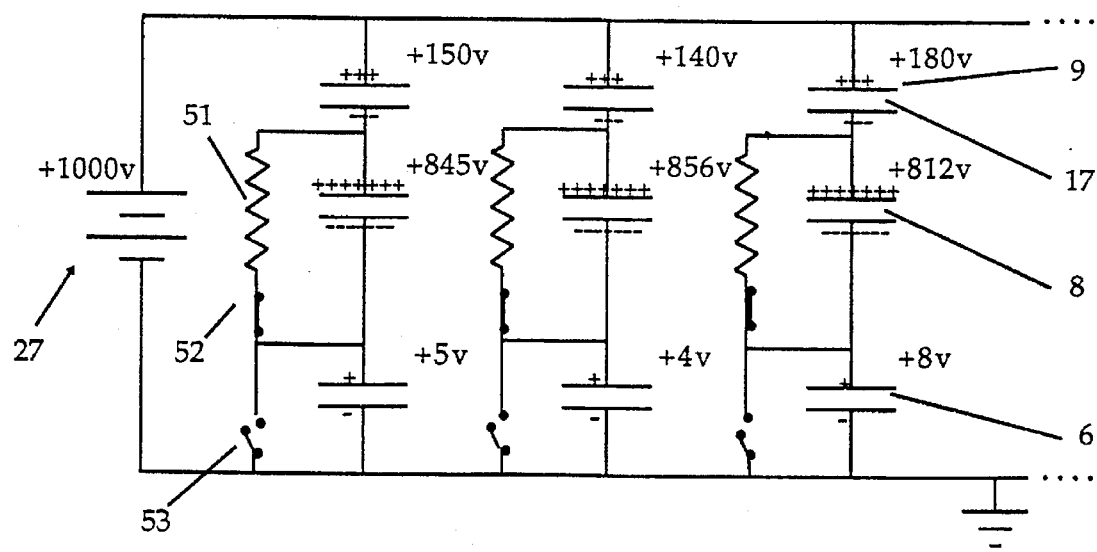
FIG. 8 represents an electrical equivalent of an X-ray image capture panel in accordance with this invention immediately after exposure to X-radiation and after the operating voltage is removed.

FIG. 8 shows the effect on the voltage redistribution pattern of different amounts of incident radiation at different pixels. During X-ray exposure image wise modulated X-radiation impinges on the panel 16. The X-rays generate excess electron hole pairs within the photoconductive layer and, in the presence of the electric field caused by the difference in voltage between the front conducting layer 9 and the outer microplates 18n, holes migrate towards the interface between the photoconductive layer 8 and the charge blocking layer 10 in the region above the inner microplates 4n. The amount of electron hole pairs generated throughout the photoconductive layer 8 is dependent on the intensity of imagewise modulated X-radiation impinging on the image capture panel 16. Positive charges accumulate across the microstorage capacitors 6 and change the voltage pattern, for instance to those voltages depicted in FIG. 8.

In the present invention, the plurality of charge barrier layers 10 and the barrier dielectric layer 17 are important features which prevent charge build-up on the charge storage capacitors 6 due to leakage current during X-ray exposure. When the positive operating voltage is applied to the top conducting layer 9, the barrier dielectric layer 17 prevents holes from being injected into the photoconductive layer from the conducting layer 9, and the charge barrier layers 10 prevent electrons from being injected into the photoconductive layer 8 from the inner microplates 4n, thereby preventing any resulting leakage current across the photoconductive layer 8 from causing additional charge build-up on the storage capacitors 6 which is not due to the X-radiation. Consequently, the resulting X-ray image is not affected by charge build-up due to leakage current, and the signal-to-noise ratio of the X-ray image is enhanced.

After a predetermined time period the X-ray flux is interrupted and X-rays no longer impinge on the element 16. The application of the initial operating voltage to the top conducting layer 9 is then removed, thus capturing a radiographic image in the element 16 in the form of stored charges in storage capacitors 6.

Referring again to FIG. 6, each of the Xn lines 11 is sequentially addressed by applying an appropriate bias voltage to the line and thus to the gate of the FETs 5 connected to the addressed Xn line 11. This renders the FETs 5 conductive and the charges stored in the corresponding charge storage capacitors 6 flow to the Yn 13 lines and to the input of charge amplifiers 33. Charge amplifiers 33 produce a voltage output proportional to the charge received on the line Yn 13. The output of the charge amplifiers 33 is digitized within the readout electronics 31, for example using A/D converters which are sequentially sampled to obtain an electrical signal representing the charge distribution in the storage capacitors 6, each value in each storage capacitor 6 representing one image pixel. After the signals from one line of pixels along an Xn line 11 are read out, the charge amplifiers are reset through reset line 39. A next Xn line 11 is addressed and the process repeated until all the charge storage capacitors have been sampled and the full image has been read out. The electrical signal output may be stored or displayed or both. Since the cassette is purposefully exposed to X-radiation, it is important to shield the electronic system 67 within the electronic cassette 20 in FIG. 1 from such radiation. This is accomplished by surrounding the electronic elements with metal foil 55 having an atomic number greater than 50, such as lead foil.

Figure 9:
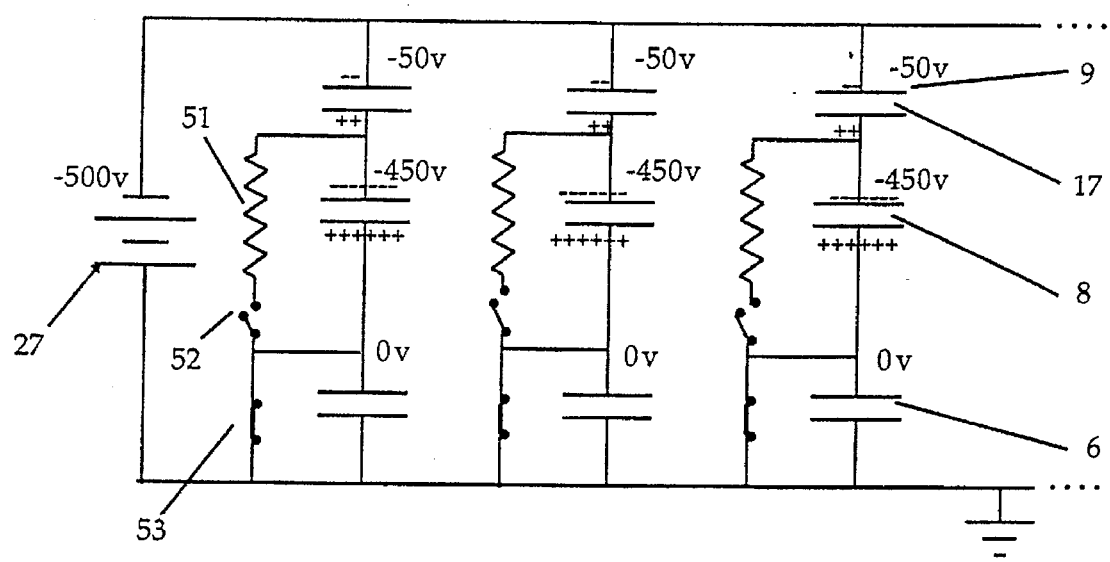
FIG. 9 represents an electrical equivalent of an X-ray image capture panel in accordance with this invention just after the bias voltage is reversed and lowered to a negative potential.

FIG. 9 shows how the panel 16 is prepared to capture additional X-ray images. After a signal has been recovered, for example using the process described, residual charges are eliminated by interconnecting all Xn lines 11 and again applying a bias voltage to the Xn lines 11 to render the transistors 5 conductive and as a result discharging completely all charge storage capacitors. All charge amplifiers 33 are reset through reset line 39. The initial operating voltage is reapplied to the front conducting panel 9, and at a controlled rate the operating voltage is reduced during a predetermined time period from the operating bias voltage to zero voltage and to a further reversed voltage which can be equal to or less than the magnitude of the original positive operating bias voltage. This reversed voltage polarity allows holes to be injected from the inner microplates 4n through the charge barrier layer 10 into the photoconductive layer 8. This movement of holes through the photoconductive layer 8 continues until the electrons previously trapped within the photoconductive layer 8 are recombined with holes, eliminating the previously retained imagewise modulated charge distribution pattern. The magnitude of the reversed polarity operating voltage is lowered over a second predetermined time period back to zero voltage. This erasing process is repeated until all the trapped charges are removed and the image capture panel prepared for subsequent image capture operations.

What is claimed is:

1. A portable electronic cassette for recording X-ray images, comprising:

a portable enclosure capable of being transported by hand, said enclosure including a first housing member having a recess therein, said first housing member being substantially transparent to X-radiation and opaque to low energy radiation and a second housing member connected to the first housing member to form a chamber between the first and second housing members;

an X-ray image capture panel disposed within the chamber for producing a plurality of electrical charges in a pattern representative of the intensity of said X-radiation;

converting means also disposed within the chamber and connected to said image capture panel for converting the plurality of electrical charges into a plurality of digitized picture element values;

memory storage means located within said cassette and connected to said converting means for receiving and storing the plurality of digitized picture element values, said memory storage means having connection means to allow access to the memory storage means; and an electrical power source disposed within said cassette and connected to said X-ray image capture panel, said converting means and said memory storage means, said electrical power source being sufficient to activate the X-ray image capture panel, the converting means and the memory storage means so that the electronic cassette is capable of being freely transported by hand.

2. A cassette in accordance with claim 1 wherein said X-ray image capture panel comprises:

a dielectric substrate layer having a top surface and a bottom surface;

a plurality of transistors arrayed adjacent the top surface of said dielectric layer;

a plurality of charge storage capacitors also arrayed adjacent the top surface of said dielectric layer, each capacitor having a conductive inner microplate connected to at least one of said transistors, said inner microplate having a top surface opposite said dielectric layer;

means disposed adjacent the top surface of said dielectric layer for electronically activating said transistors and individually accessing each of said capacitors;

a photoconductive layer disposed over said transistors and said means for activating and accessing;

a top conducting layer disposed over said photoconductive layer opposite said dielectric layer;

a plurality of charge barrier layers disposed adjacent, respectively, the top surface of each of said inner microplates; and a barrier dielectric layer disposed between and coextensive with said photoconductive layer and said top conducting layer.

3. A cassette in accordance with claim 2 wherein said layer of photoconductive material is chosen from the group consisting of amorphous selenium, lead oxide, cadmium sulfide, and mercuric iodide.

4. A cassette in accordance with claim 2 wherein each capacitor also comprises a conductive outer microplate disposed on the top surface of said dielectric layer, and dielectric material disposed over said outer microplate, said inner microplate being disposed over said dielectric material opposite said outer microplate.

5. A cassette in accordance with claim 1 further including means for erasing the plurality of electrical charges within said image capture panel.

6. A cassette in accordance with claim 5 further including a radiation shielding element positioned around the converting means, the memory storage means, the charge erasing means and the electrical power source.

7. A cassette in accordance with claim 1 wherein said memory storage means for storing a plurality of digitized picture element values comprises means for storing at least one exposure of the cassette to incident radiation.

8. A cassette in accordance with claim 1 wherein said memory storage means is selected from the group consisting of a random-access-memory integrated-circuit device, a magnetic disk recording device, and an optical disk recording device.

9. A cassette in accordance with claim 1 wherein said electrical power source comprises a battery.

10. A cassette in accordance with claim 1 having an X-radiation sensor mounted on said first housing member for detecting the onset and absence of impinging radiation and for activating said image capture panel, said converting means and said memory storage means.

11. A cassette in accordance with claim 1 wherein said first and second housing members have a structure capable of supporting a human body.

12. A method for capturing an X-ray radiogram, comprising:

placing a portable electronic cassette having an X-ray image capture panel disposed within said cassette in a first radiation imaging location located in close proximity to a first human body said cassette having a first housing member being positioned adjacent said body and being substantially transparent to X-radiation;

impinging the first housing member of the electronic cassette with imagewise modulated X-radiation;

producing an imagewise modulated pattern of electrical charges within said X-ray image capture panel disposed within said cassette;

converting the pattern of electrical charges into digitized picture element values representing the distribution and magnitude of electrical charges produced within the X-ray image capture panel;

preserving said digitized picture element values in memory storage means;

neutralizing the electrical charges remaining within the X-ray image capture panel so that the imagewise modulated pattern is eliminated; and, transporting by hand the portable electronic cassette to a second radiation imaging location located in close proximity to a second human body, said second human body being the same or different from said first human body without removing the image capture panel from said cassette or reading out from said cassette the digitized picture element values.

13. A method for capturing an X-ray radiogram in accordance with claim 12 further comprising repeating said placing, impinging, producing, converting, preserving, neutralizing and transporting steps.

* * * * *